United States Patent [19]

Baranowitz et al.

[11] Patent Number: 5,310,764
[45] Date of Patent: May 10, 1994

[54] TREATMENT OF AGE RELATED MACULAR DEGENERATION WITH BETA-CAROTENE

[76] Inventors: Steven Baranowitz, 85 Tices La. - Apt. 39, East Brunswick, N.J. 08816; Andrew Brookner, 25 Spenser Dr., Short Hills, N.J. 07078

[21] Appl. No.: 880,709

[22] Filed: May 8, 1992

[51] Int. Cl.⁵ ............................................ A67K 31/07
[52] U.S. Cl. ..................................... 514/725; 514/912
[58] Field of Search ................................. 514/725, 912

[56] References Cited

PUBLICATIONS

Health Periodicals Abstract of Western Journal of Medicine, vol. 155 Issue No. 4, Oct. 1991.
Kennekens et al. Federal Research in Progesss. (The Research started on 1984).
Steven A. Baranowitz, "Regeneration, Neural Crest Derivatives and Retinoids: A New Synthesis," *J. Theor. Biol.*, 140: 231-242, 1989.
Garry J. Handelman et al., "Carotenoids in the Human Macula and Whole Retina," *Investigative Ophthalmology*, 29:850-855, 1988.
Richard W. Young, "Solar Radiation and Age-related Macular Degeneration," *Survey of Ophthalmology*, 32:252-269, Jan.-Feb., 1988.
Richard W. Young, "Pathophysiology of Age-related Macular Degeneration," *Survey of Ophthalmology*, 31:291-306, 1987.
Susan B. Bressler et al. "Relationship of Drusen and Abnormalities of the Retinal Pigment Epithelium to the Prognosis of Newvascular Macular Degeneration," *Arch Ophthalmol*, 108:1442-1447, Oct., 1990.
Neil M. Bressler et al., "Age-related Macular Degeneration," *Survey of Ophthalomology*, 32:375-413, May-Jun., 1988.
Howard Schatz et al., "Atrophic Macular Degeneration Rate of Spread of Geographic Atrophy and Visual Loss," *Ophthalmology*, 96:1541-1551, 1989.
J. P. Sarks et al., "Evolution of Geographic Atrophy of the Retinal Pigment Epithelium," *Eye*, 2:552-577, 1988.
D. Pauleikhoff et al., "Drusen as Risk Factors in Age-Related Macular Disease," *American Journal of Ophthmology*, 109:38-43, Jan., 1990.
W. T. Ham Jr. et al., "Basic Mechanisms Underlying the Production of Photochemical Lesions in Mammalian Retina," *Current Eye Research*, 3:165-174, 1984.
M. L. Katz et al., "Fluorescent Pigment Accumulation in Retinal Pigment Epithelium of Antioxidant-Deficient Rats," *Investigative Ophthalmology*, 17: 1049-1058, 1978.
Martin L. Katz et al., "Relationship Between Dietary Retinol and Lipofuscin in the Retinal Pigment Epithelium," *Mechanisms of Ageing and Development*, 35:291-305, 1986.
Martin L. Katz et al., "Development of Lipofuscin--Like Fluorescence in the Retinal Pigment Epithelium in Response to Protease Inhibitor Treatment," *Mechanisms of Ageing and Development*, 49:23-40, 1989.
C. Kathleen Dorey et al., "Cell Loss in the Aging Retina," *Investigative Ophthalmology*, 30: 1691-1699, 1989.
Glenn L. Wing et al., "Topography and Age Relationship of Lipofuscin Concentration in the Retinal Pigment Epithelium," *Investigative Ophthalmology*, 17, 601-607, 1977.
Sheila K. West et al., "Exposure to Sunlight and Other Risk Factors for Age-Related Macular Degeneration," *Arch Ophthalmol*, 107:875-879, Jun., 1989.
Mike Boulton et al., "The Formation of Autofluores- (List continued on next page.)

Primary Examiner—Zohreh A. Fay
Attorney, Agent, or Firm—Darby & Darby

[57] ABSTRACT

According to the present invention, there are provided methods for treating age related macular degeneration in a mammal; for preventing impairment of the vision or for improving impaired vision of a mammal whose eye has drusen; for preventing formation or growth of drusen in the eye of a mammal; and for reducing the number or the size of drusen or for fading drusen without resultant areas of retinal atrophy, without resultant impairment of vision, or without a combination of the foregoing in the eye of a mammal. Beta-carotene in appropriate amounts is administered to the mammal.

19 Claims, 1 Drawing Sheet

OTHER PUBLICATIONS cent Granules in Cultured Human RPE," *Investigative Ophthalmology*, 30:82–89, 1989.

Mike Boulton et al., "Age-Related Changes in the Morphology, Absorption and Fluorescence of Melanosomes and Lipofuscin Granules of the Retinal Pigment Epithelium," *Visioin Research*, 30:1291–1303, 1990.

John D. Gottsch et al., "Hematogenous Photosensitization," *Investigative Ophthalmology*, 31:1674–1683, Sep., 1990.

David A. Newsome et al., "Oral Zinc in Macular Degeneration," *Arch Ophthalmol*, 106:192–198, Feb., 1988.

Sohrab Mobarhan et al., "Effects of $\beta$-Carotene Repletion on $\beta$-Carotene Absorption, Lipid Peroxidation, and Neutrophil Superoxide Formation in Young Men," *Nutrition & Cancer*, 14:195–206, 1990.

Shirley H. Sarks et al., "Age-related Macular Degeneration: Atrophic Form," *Retina*, Chapter 64, 2:149–173, 1989.

Peter A. Campochiaro et al., "Retinoic Acid Promotes Density-Dependent Growth Arrest in Human Retinal Pigment Epithelial Cells," *Investigative Ophthmology*, 32:65–72, 1991.

R. J. Stephens et al., "Vitamin E Distribution in Ocular Tissues Following Long-Term Dietary Depletion and Supplementation as Determined by Microdissection and Gas Chromatography-Mass Spectrometry," *Exp. Eye Research*, 47:237–245, 1988.

Craig E. Eldred, "Vitamins A and E in RPE Lipofuscin Formation and Implications For Age-Related Macular Degeneration," *Inherited and Environmentally Induced Retinal Degenerations*, pp. 113–129, 1989.

John J. Weiter, "Macular Degeneration", *Arch. Ophthalmol*, 106:183–198, Feb., 1988.

Theo L. van der Schaft, et al., "Is Basal Laminar Deposit Unique for Age-Related Macular Degeneration?" *Arch. Ophthalmol*, 109:420–425, Mar., 1991.

TREATMENT OF AGE RELATED MACULAR DEGENERATION WITH BETA-CAROTENE

FIELD OF THE INVENTION

The invention relates to a method for the treatment of age related macular degeneration (ARMD) in the eyes of mammals. Beta-carotene is administered, preferably systemically, in a therapeutically effective amount.

The administration of beta-carotene has also been found to prevent the growth or the formation of drusen, to reduce the number or the size of drusen, or to cause drusen to fade without resultant retinal atrophy or impairment of vision.

BACKGROUND OF THE INVENTION

Age related macular degeneration is a common degenerative disease of the retina and is the leading cause of blindness in the elderly. The disease is associated with chronological age, as ten percent of the individuals between the ages of sixty-five and seventy-five in the United States have lost some vision because of the disease. Thirty percent of people over the age of seventy-five have lost some vision due to the disease. Young, "Pathophysiology of Age-related Macular Degeneration", *Survey of Ophthalmology*, Vol. 31, No. 5, March-April 1987.

The basic anatomy of the eye is illustrated in FIG. 1.

The sclera (1) forms the external tissue of the eyeball. The choroid (3) is the vascular layer beneath the sclera. The retina (5) lines the choroid (3) and is the nervous membrane upon the surface of which the images of external objects are received and then are transmitted through the optic nerve (11). Precisely in the center of the posterior part of the retina, corresponding to the axis of the eye, and at a point in which the sense of vision is perfect in a normal eye, is a yellowish area called the macula (7) which has a central depression, called the fovea (9). FIG. 2 illustrates that beneath the sensory retina is a single layer of pigmented epithelial cells called the retinal pigment epithelium (RPE) (1). Between the RPE and the choriocapillaries is a membrane known as Bruch's membrane (7).

ARMD is believed to be caused by the deterioration and death of the retinal pigment epithelium. The cause of the degeneration is unknown, but it has been speculated that ARMD may be an advanced stage of the normal aging process. Young, *Survey of Ophthalmology*, Vol. 31, No. 5, March-April 1987. The variability in the age of onset of the disease is likely due to the variability in biological aging.

The earliest and most obvious clinical sign of ARMD is the presence of drusen. Sarks et al. "Age-related Macular Degeneration: Atrophic Form", *Retina*, Vol. 2., The C. V. Mosby Company, 1989. Drusen are extracellular masses of heterogeneous composition containing materials excreted from aging RPE cells and remnants of dead cells. Young, *Survey of Ophthalmology*, Vol. 31, No. 5, March-April 1987. They are situated between the basal membrane of the RPE and Bruch's membrane. Young, *Survey of Ophthalmology*, Vol. 31, No. 5, March-April 1987. Clinically, drusen are seen as localized yellowish deposits or excrescences lying deep to the retina. Bressler et al. "Age-related Macular Degeneration", *Survey of Ophthalmology*, Vol. 32, No. 6, May-June 1988.

Small discrete drusen, i.e. hard drusen, are seen in eighty-three percent of normal adult eyes. Hard drusen represent a localized disorder of only a few RPE cells. The RPE cells overlying the drusen are often thinned or pigmented. Bressler et al., *Survey of Ophthalmology*, Vol. 32, No. 6, May-June 1988.

Larger areas of RPE dysfunction having ill defined, nondiscrete boundaries are termed soft drusen. Soft drusen are associated with more serious forms of ARMD in which there is significant loss of central vision. Soft drusen often merge into one another and become confluent.

The interface between the choroid and the retina, the development of drusen, and the changes induced by drusen are illustrated in FIG. 2. On the far left, the retinal pigment epithelium (RPE) cells (1) contain only a few residual bodies (3), and these are largely confined to the base of the cells. Melanin granules (5) are present near the apical surface. Bruch's membrane (7) is thin and uncontaminated. The visual cells (9) (of which only the inner and outer segments are shown) are regularly aligned and densely packed. This is the typical appearance in young eyes. In the adjacent region, early senescent changes are shown: the number of residual bodies (3) has increased throughout the RPE (1) cytoplasm, and Bruch's membrane (7) has thickened. To the right, a druse (11) has been formed. On the surface of the druse, the attenuated RPE cells are engorged with residual bodies, melanin has diminished in amount, some of the visual cells have disappeared, and the remainder are physically distorted. Surviving rods and cones become shorter and broader as adjacent cells disappear.

Patients can still have excellent visual acuity in the early stages of ARMD. Bressler et al., *Survey of Ophthalmology*, Vol. 32, No. 6, May-June 1988.

Loss of central vision can be attributed to several different occurrences, all of which relate to the drusen. Vision loss can occur when RPE and photoreceptor cells over the drusen degenerate and debris accumulates. Although the drusen fade and ultimately disappear, areas of atrophy remain. This fading is believed to be due to the activity of macrophages and adjacent RPE cells. This form of ARMD is termed geographic atrophy. Sarks et al., "Evolution of Geographic Atrophy of the Retinal Pigment Epithelium", *Eye*, Vol. 2, 552-577, 1988; see also Schatz et al., "Atrophic Macular Degeneration", *Ophthalmology*, 96, October 1989.

Soft drusen can also cause vision loss by initiating breaks in Bruch's membrane which allow the egress of fibrovascular tissue from the choriocapillaries. The fibrous tissue can lead to serous or hemorrhagic detachments of the sensory retina with accompanying severe loss of central vision.

Finally, drusen may become so abundant as to involve the fovea, interrupting the function of the sensory retina and resulting in vision loss.

Research on the effects of phototoxicity in human and primate retinas has demonstrated some relationship between acute photic damage to the retina and the changes symptomatic of ARMD. Young, "Solar Radiation and Age-related Macular Degeneration", *Survey of Ophthalmology*, Vol. 32, No. 4, January-February 1988. However, if ARMD were caused by chronic phototoxicity, one would expect an association between life-long light exposure and the prevalence of ARMD. Recent epidemiological studies indicate that there is no correlation between ARMD and the cumulative exposure of UV light. West et al., "Exposure to Sunlight and Other Risk Factors for Age-related Macular Degeneration", *Arch. Ophthalmol.*, Vol. 107, June 1989.

Furthermore, various studies have been proposed or performed to determine the ediology of ARMD. Handleman et al., "Carotenoids in the Human Macula and Whole Retina", *Investigative Ophthalmology and Visual Science*, Vol. 29, No. 6, 850–855, June 1988, found that the major carotenoids in the retina were lutea and zeaxanthin. No beta-carotene was found in the retina. Handleman et al. proposed to prevent ARMD through the use of retinal carotenoids to confer antioxidant protection. Handleman et al. classified carotenoids as protective agents against highly reactive singlet oxygen and proposed that singlet oxygen-induced liquid peroxidation was a mediator of light damage in the retina. Carotenoid deficient monkeys were reported to show pigment changes in the fundus.

Ham et al., "Basic Mechanisms Underlying the Production of Photochemical Lesions in the Mammalian Retina", *Current Eye Research*, Vol.3, No. 1, 165–174, 1984, disclose that both vitamin E and beta-carotene are naturally occurring singlet oxygen quenchers and that the toxic combination of light and oxygen leads to the generation of free radicals, a possible cause of phototoxicity.

Vitamin E was suggested to be a likely vitamin A autoxidation inhibitor by Katz et al., "Relationship between Dietary Retinol and Lipofuscin in the Retinal Pigment Epithelium", *Mechanisms of Aging and Development*, Vol. 35, 291–305, 1986. See also Katz et al. "Development of Lipofuscin-like Fluorescence in the Retinal Pigment Epithelium in Response to Protease Inhibitor Treatment", *Mechanisms of Aging and Development*, Vol. 49, 23–40, 1989; Stephens et al., "Vitamin E Distribution in Ocular Tissues Following Long-term Dietary Depletion and Supplementation as Determined by Microdissection and Gas Chromatography-Mass Spectrometry", *Experimental Eye Research*, Vol. 47, 237–245, 1988.

Retinoids have been demonstrated to modulate the growth and differentiation of several types of cells by Campochiaro et al., "Retinoic Acid Promotes Density-Dependent Growth Arrest in Human Retinal Pigment Epithelial Cells", *Investigative Ophthalmology and Visual Science*, Vol. 32, No. 1, January 1991.

Gottsch et al., "Hematogenous Photosensitization", *Investigative Ophthalmology and Visual Science*. Vol. 31, No. 9, September 1990, hypothesize that tissue damage due to photosensitization which in turn is due to free radical generation, may be prevented either by inducing protective enzymes using scavengers of free radicals and singlet oxygen such as vitamin E or by filtering the appropriate excitatory wavelengths. See also Boulton et al., "The Formulation of Autofluorescent Granules in Cultured Human RPE", *Investigative Ophthalmology and Visual Science*. Vol. 30, No. 1, January 1989. While Gottsch et al. suggest that beta-carotene and vitamin E are singlet oxygen quenchers, they strongly suggest that treatment of established disease is not aided by these agents and that prophylaxis by vitamin E is not always effective.

Katz et al. "Flourescent Pigment Accumulation in Retinal Pigment Epithelium of Antioxidant-Deficient Rats", *Investigative Ophthalmology Visual.*, 1049–1058, 1978, disclose that lipofuscin pigment in rats may be attributable to a diet that produces physiological antioxidant deficiency. Young, *Survey of Ophthalmology*, Vol. 32, No. 4, January-February 1988, discloses that beta-carotene can diminish photodynamic change in the retina. However, treatment of established ARMD is not disclosed, and no relationship between the presence or the growth of drusen and photodynamic damage is suggested.

Because the normal retina has a high concentration of zinc, supplemental zinc was investigated in the treatment of ARMD by Newsome et al. "Oral Zinc in Macular Degeneration", *Arch. Ophthalmology*, Vol. 106, February 1988. No correlation of ARMD with initial serum levels of zinc was observed, and progression of the disease was seen in both the treatment and the non-treatment groups. Furthermore, zinc ingestion can be accompanied by serious side effects.

It has now been discovered that the administration of appropriate amounts of beta-carotene can successfully treat ARMD. Beta-carotene had also proven useful in the inhibition and resolution of drusen, particularly without typical vision impairment or detrimental anatomical and physiological changes in the eye.

SUMMARY OF THE INVENTION

Figure 1:
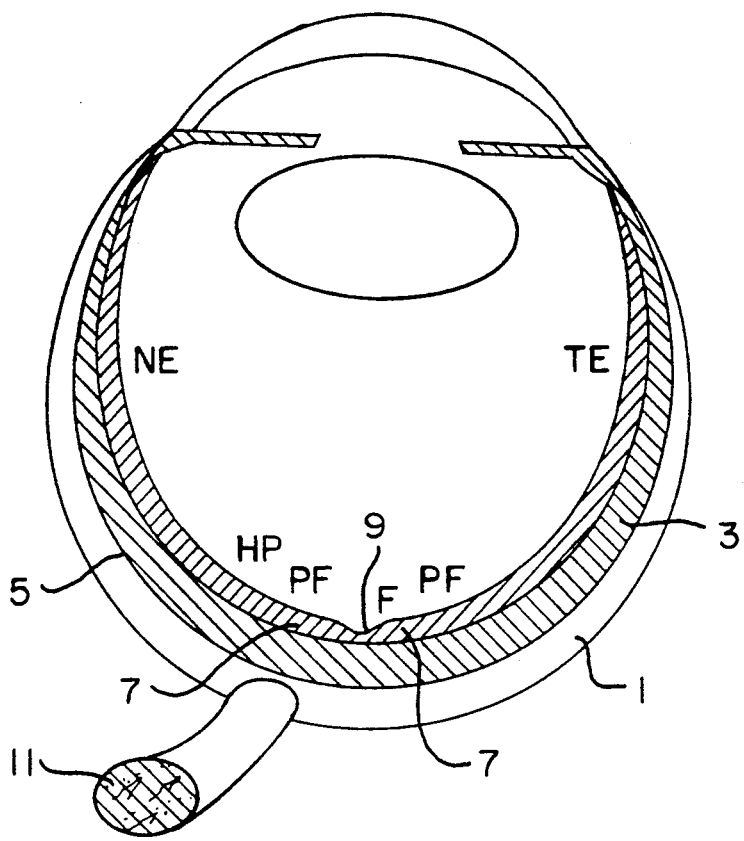
FIG. 1 is a diagram of the anatomy of the eye.
Figure 2:
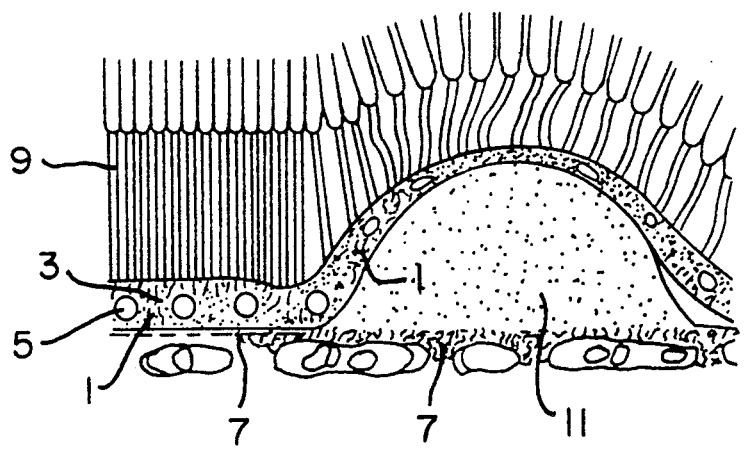
FIG. 2 is a diagram of the development of drusen.

According to the present invention, there is provided a method for treating age related macular degeneration in a mammal comprising administering to the mammal, a therapeutically effective amount of beta-carotene.

The invention also contemplates a method for preventing impairment of the vision or for improving impaired vision of a mammal whose eye has drusen comprising administering to the mammal a therapeutically effective amount of beta-carotene.

In a further embodiment, a method for preventing formation or growth of drusen in the eye of a mammal is provided. This method comprises administering to the mammal a drusen inhibiting effective amount of beta-carotene.

Furthermore, a method for reducing the number or the size of drusen or for fading drusen without resultant areas of retinal atrophy, without resultant impairment of vision, or without a combination of the foregoing in the eye of a mammal is provided. Beta-carotene in a drusen reducing amount is administered to the mammal.

DETAILED DESCRIPTION OF THE INVENTION

Carotinoids are terpenes that are widely distributed in the plant and animal kingdoms. Beta-carotene is a common carotinoid having the chemical structure:

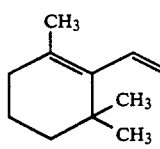 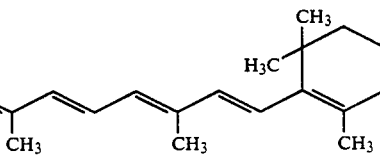

Beta-carotene, in mammals, readily undergoes oxidative cleavage at the central double bond to give two equivalents of the aldehyde retinol. Biochemical reduction of the aldehyde carbon yields vitamin A.

Age related macular degeneration is a disease predominantly of humans. The most disturbing symptoms of ARMD include a slow or sudden loss of central vision or vision distortion in one eye. However, ARMD is diagnosed by the visualization of drusen in the eye coupled with this vision loss.

The diagnosis of ARMD is typically made by funduscopy which reveals a pigmentary or hemorrhagic disturbance due to drusen in the macular region of the involved eye. The contralateral eye almost always shows some pigmentary disturbance and the presence of drusen in the macula. Fluorescein angiography can also be utilized in the diagnosis of ARMD. This procedure visualizes the neovascular membranes beneath the retina.

Although the mere presence of drusen is not definitive of ARMD, typically, the presence of drusen will lead to the disease. Therefore, it is advantageous to be able to treat the presence of drusen by reducing the size or the amount of drusen or by fading the drusen before and without clinical impairment of vision due to the disease.

Typically, drusen will grow or fade leaving resultant areas of retinal atrophy. This retinal atrophy leads to vision loss. Drusen can cause vision loss through other mechanisms, however. Drusen can cause degeneration of the retinal pigment epithelial cells, photoreceptor cells, or a combination thereof. Visual impairment can also be due to one or more breaks in the Bruch's membrane which permit the egress of fibrovascular tissues from choriocapillaries. Finally, the vision impairment can be due to the formation or growth of drusen itself which becomes sufficient to cover a significant portion of the fovea.

Applicants hypothesize, without being bound to any particular theory, that by increasing the availability of carotinoids, and particularly beta-carotene, to the retinal pigment epithelium, function can be normalized. In fact, it has been suspected for some time that carotinoids are present in the human eye as reflected by the term macula lutea, lutea meaning yellow.

In all of the embodiments of the present invention, beta-carotene is preferably administered systemically. Systemic administration most preferably is by the oral route.

The term "daily dosage" identifies the average amount of beta-carotene administered to a patient. However, the dosage need not be administered daily. The daily dosage is merely an average dosage that a patient receives when beta-carotene is administered over a period. The daily dosage can be administered in divided portions so that the total amount administered is the daily dosage. Typically, acceptable blood levels of beta-carotene and chemically detectable changes in blood levels will be achieved after administration of beta-carotene in the prescribed amounts for several months, i.e. three to six months.

Although the safe upper limit of the amount of beta-carotene that can be administered to a human has not yet been determined, it is believed that such an upper limit is at least 1000 mg/day.

In the treatment of age related macular degeneration or in the prevention or improvement of impaired vision in an eye with drusen, beta-carotene is administered in a therapeutically effective amount. Therapeutically effective amounts of beta-carotene are those amounts sufficient to stabilize the progression of the disease or to resolve the symptoms of ARMD. This amount will depend upon the age, weight, sex, sensitivity, and the like of the individual. In many mammals, the therapeutically effective amount can be determined by experimentation well known in the art such as by establishing a matrix of dosages and frequencies and assigning a group of experimental subjects to each point in the matrix.

Typically for a human being, that amount will be at least about 50 mg/day of beta-carotene. Most preferably, that amount will range from about 60 mg/day to about 350 mg/day. Particularly, the dosage will be about 240 mg/day.

The amount of beta-carotene required to prevent formation or growth of drusen is a drusen inhibiting amount of beta-carotene. Again, this amount will depend upon the age, weight, sex, sensitivity, and the like of the individual. This amount can be determined experimentally as explained above. Preferably, drusen inhibiting amounts of beta-carotene will be at least about 50 mg/day. Most preferably, that amount will range from about 60 mg/day to about 350 mg/day. Particularly, the dosage will be about 240 mg/day.

The amount of beta-carotene required to reduce the number or the size of drusen or to fade drusen is a drusen reducing amount of beta-carotene. Again that amount may be determined experimentally as explained above. Typically for a human being, that amount will be at least about 50 mg/day. Most preferably, that amount ranges from about 60 mg/day to about 350 mg/day. Particularly, the dosage will be about 240 mg/day.

Although beta-carotene is provided through normal diet, the amounts of beta-carotene useful in the present invention typically are not provided by normal diet. This is because the foods that supply beta-carotene in the normal diet contain various other substances. If sufficient amounts of these foods were consumed to provide the necessary amounts of beta-carotene, these other substances would have been consumed in toxic amounts. Therefore, beta-carotene is typically supplied in the methods of the present invention through supplementation. Commercially available forms of beta-carotene are available, for example, from Hoffman-LaRoche under the trademark SOLATENE TM or as "beta-carotene".

Typically, a course of administration will last for about three months to several years and preferably to about three years. If new or further impairment of vision, development or growth of drusen, or symptoms of the disease occur in a subject who has been treated according to the present invention, it may become necessary to repeat the administration, to adjust the dosage of beta-carotene, or to administer a maintenance effective amount of beta-carotene. This maintenance effective amount of beta-carotene will be that amount which will prevent regression to pretreatment conditions. This amount may be the same as or less than the amount used during treatment.

DESCRIPTION OF THE PREFERRED EMBODIMENTS

The following examples illustrate the invention without limitation. Drusen are counted from funduscopy photographs and are counted as lighter areas proximate to the fovea.

EXAMPLE 1

An 87 year old male was initially diagnosed as having bilateral cataracts and ARMD. The patient underwent cataract surgery on one eye about one year after the initial diagnosis and underwent cataract surgery on the other eye about one year after the first surgery.

About one year and two months after the last surgery (Examination 1), funduscopy revealed a large number of drusen in each eye. One year and two months later, (Examination 2), visual acuity was measured as 20/20 in the right eye and 20/30 in the left eye. The patient was placed on a regimen of 60 mg/day of beta-carotene.

About one month later (Examination 3), visual acuity was measured as 20/25 in the right eye and 20/30 in the left eye. The patient was placed on a regimen of 120 mg/day of beta-carotene. About one month later (Examination 4), visual acuity was measured at 20/30 in the right eye and 20/30 in the left eye. The patient was placed on a regimen of 180 mg/day of beta-carotene. About one month later, (Examination 5), visual acuity was measured as 20/25 in the right eye and 20/30 in the left eye. The patient was placed on a regimen of 240 mg/day of beta-carotene.

Visual acuity was measured periodically over the next three months and ranged from 20/20 to 20/25 in the right eye and 20/25 to 20/30 in the left eye, while the patient was maintained on the 240 mg/day beta-carotene regimen. Funduscopy at the end of this period (Examination 6), revealed a 35.8 percent decrease in the number of drusen in one eye and a 68.7 percent decrease in the number of drusen in the other eye. The decrease in drusen was determined by comparing the number of drusen seen at Examination 1 and Examination 6. Many drusen also decreased in size during this period. Initial and final drusen counts are compared in Table 1.

EXAMPLE 2

An 84 year old female was initially diagnosed as having bilateral cataracts and ARMD. The patient underwent cataract surgery on the left eye two weeks after the diagnosis and underwent cataract surgery on the right eye approximately two and one half months after the first surgery. Branch vein occlusion was diagnosed in the left eye about one year and two months after the initial diagnosis, and central vein occlusion was diagnosed in the left eye about four months subsequently. About three years after the initial diagnosis of ARMD (Examination 1), visual acuity was measured as 20/100 in the right eye and count fingers vision in the left eye. The patient was placed on a regimen of 60 mg/day of beta-carotene.

About one month later (Examination 2), visual acuity was measured as 20/200 in the right eye and count fingers vision in the left eye. The patient was placed on a regimen of 120 mg/day of beta-carotene.

About month later (Examination 3), visual acuity was measured as 20/70 in the right eye and count fingers vision in the left eye. Funduscopy revealed a concentration of drusen in the foveal area of one eye. The patient was placed on a regimen of 180 mg/day of beta-carotene.

About month later (Examination 4) visual acuity was measured as 20/70 in the right eye and count fingers vision in the left eye. The patient was placed on a regimen of 240 mg/day of beta-carotene.

Visual acuity was measured periodically over the next four months and ranged from 20/70 to 20/80 in the right eye and remained count fingers vision in the left eye, while the patient was maintained on a regimen of 240 mg/day of beta-carotene. Later, visual acuity in the right eye was 20/80 and count fingers vision in the left eye.

Funduscopy at the end of this period (Examination 5), revealed a 90.9 percent decrease in drusen in the eye previously photographed, a sharp reduction in the foveal region. The decrease in drusen was determined by comparing the number of drusen seen at Examination 3 and Examination 5. Initial and final drusen counts are compared in Table 1.

EXAMPLE 3

A 70 year old female was initially diagnosed as having bilateral cataracts and ARMD. The patient underwent cataract surgery on the left eye about ten months later. About one year after surgery (Examination 1), visual acuity was measured as 20/25 in the right eye and 20/20 in the left eye. Funduscopy revealed the presence of drusen in the foveal region of one eye. The patient was placed on a regimen of 60 mg/day of beta-carotene.

About one month later (Examination 2), visual acuity was measured as 20/30 in the right eye and 20/20 in the left eye. The patient was continued on the same regimen of beta-carotene.

About one and one half months later (Examination 3), visual acuity was measured as 20/30 in the right eye and 20/20 in the left eye. The patient was placed on a regimen of 120 mg/day of beta-carotene.

About one month later (Examination 4), visual acuity was measured as 20/25 in the right eye and 20/20 in the left eye. Funduscopy revealed a 25 percent decrease in the number of drusen and a marked decrease in the amount of drusen in the foveal area of the eye previously photographed. The decrease in drusen was determined by comparing the number of drusen seen at Examination 1 and Examination 4. The patient was placed on a regimen of 180 mg/day of beta-carotene. Initial and final drusen counts are compared in Table 1.

One and one half months later, visual acuity in the left eye was measured as 20/30 and visual acuity in the right eye was measured as 20/20. The patient was placed on a regimen of 240 mg/day of beta-carotene.

EXAMPLE 4

An 86 year old male was initially diagnosed as having bilateral cataracts and ARMD. The patient underwent cataract surgery in the right eye, about five months after the initial diagnosis. Three years and three months after the initial visit (Examination 1), the patient's visual acuity was measured as 20/40 in the right eye and 20/40 in the left eye. Funduscopy revealed the presence of drusen in the foveal area of one eye.

About two months later (Examination 2), visual acuity was measured as 20/30 in the right eye and 20/30 in the left eye. The patient was placed on a regimen of 180 mg/day of beta-carotene.

About one month later (Examination 3), visual acuity was measured as 20/40 in the right eye and 20/30 in the left eye. Funduscopy revealed an increase in the amount of drusen in the foveal area of the eye previously photographed. The patient was placed on a regimen of 240 mg/day of beta-carotene.

Over about the following four months visual acuity ranged from 20/30 to 20/40 in the right eye and 20/30 to 20/40 in the left eye, while the patient was maintained on a dosage of 240 mg/day of beta-carotene.

About one month after this period (Examination 4), visual acuity was measured as 20/40 in the right eye and 20/40 in the left eye. Funduscopy revealed a 40 percent decrease in the amount of drusen in the eye previously photographed. The decrease was determined by comparing the number of drusen seen at Examination 1 and Examination 4. The patient was maintained on the regimen of 240 mg/day of beta-carotene. Initial and final drusen counts are compared in Table 1.

Examples 1-4 demonstrate the remarkable transformation of and reduction in number and size of drusen as well as the successful treatment of ARMD due to beta-carotene administration in accordance with the present invention.

TABLE 1

| Example | 1 | | 2 | 3 | 4 |
|---|---|---|---|---|---|
| | First Eye | Second Eye | | | |
| Initial Drusen Count | 162 | 131 | 11 | 12 | 15 |
| Final Drusen Count | 104 | 41 | 1 | 9 | 9 |
| % Decrease | 35.8 | 68.7 | 90.9 | 25 | 40 |

The above-mentioned patents, test methods, and publications are hereby incorporated by reference.

Many variations of the present invention will suggest themselves to those skilled in the art in light of the above detailed description. For example, beta-carotene can be coupled with the administration of other medications to treat other ailments of the eye in conjunction with the treatment of ARMD. All such obvious variations are within the intended scope of the appended claims.

We claim:

1. A method for preventing impairment of the vision or for improving impaired vision of a mammal whose eye has drusen comprising administering to said mammal, a therapeutically effect amount of beta-carotene.

2. A method as defined in claim 1, wherein said impairment of vision is due to the degeneration of retinal pigment epithelium cells, photoreceptor cells, or a combination thereof.

3. A method as defined in claim 1, wherein said impairment of vision is due to retinal atrophy.

4. A method as defined in claim 1, wherein said impairment of vision is due to one or more breaks in Bruch's membrane.

5. A method as defined in claim 4, wherein said break results in the egress of fibrovascular tissue from choriocapillaries in said eye.

6. A method as defined in claim 1, wherein said impairment of vision is due to the formation or growth of drusen.

7. A method as defined in claim 1, wherein said therapeutically effective amount of beta-carotene comprises at least about 50 mg/day of beta-carotene.

8. A method as defined in claim 7, wherein said therapeutically effective amount of beta-carotene comprises from about 60 mg/day to about 350 mg/day of beta-carotene.

9. A method as defined in claim 8, wherein said therapeutically effective amount of beta-carotene comprises about 240 mg/day of beta-carotene.

10. A method as defined in claim 1, wherein said administering is systemic.

11. A method as defined in claim 10, wherein said administering is oral.

12. A method as defined in claim 1, wherein said drusen is selected from the group consisting of hard drusen, soft drusen, or a combination thereof.

13. A method for reducing the number or the size of drusen or for fading drusen without resultant areas of retinal atrophy in animal whose eye has drusen, without resultant impairment of vision, or without a combination of the foregoing in the eye of a mammal, said method comprising administering to said mammal, a drusen reducing amount of beta-carotene.

14. A method as defined in claim 13, wherein said drusen reducing amount of beta-carotene comprises at least about 50 mg/day.

15. A method as defined in claim 14, wherein said drusen reducing amount of beta-carotene comprises from about 60 mg/day to about 350 mg/day.

16. A method as defined in claim 15, wherein said drusen reducing amount of beta-carotene comprises about 240 mg/day.

17. A method as defined in claim 13, wherein said administering is systemic.

18. A method as defined in claim 17, wherein said administering is oral.

19. A method as defined in claim 13, wherein said drusen is selected from the group consisting of hard drusen, soft drusen, or a combination thereof.

* * * * *